US00PP23493P2

(12) United States Plant Patent
Blom

(10) Patent No.: US PP23,493 P2
(45) Date of Patent: Mar. 19, 2013

(54) ***ECHINACEA* PLANT NAMED 'SOUTHERN BELLE'**

(50) Latin Name: *Echinacea hybrida*
Varietal Denomination: Southern Belle

(76) Inventor: Arie Blom, Oudewater (NL)

( * ) Notice: Subject to any disclaimer, the term of this patent is extended or adjusted under 35 U.S.C. 154(b) by 101 days.

(21) Appl. No.: 13/068,696

(22) Filed: May 17, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — C. A. Whealy

(57) ABSTRACT

A new and distinct cultivar of *Echinacea* plant named 'Southern Belle', characterized by its upright plant habit; vigorous growth habit; freely basal branching habit; strong flowering stems; early and freely flowering habit; long flowering period; large anemone-type inflorescences with red purple-colored ray and disc florets; and good garden performance.

3 Drawing Sheets

Botanical designation: *Echinacea hybrida.*
Cultivar denomination: 'Southern Belle'.

BACKGROUND OF THE INVENTION

The present invention relates to a new and distinct cultivar of *Echinacea* plant, botanically known as *Echinacea hybrida*, and hereinafter referred to by the name 'Southern Belle'.

The new *Echinacea* plant is a product of a planned breeding program conducted by the Inventor in Vleuten and Zuidwolde, The Netherlands. The objective of the breeding program is to develop new freely branching and freely flowering *Echinacea* plants with large centers and attractive ray and disc floret coloration.

The new *Echinacea* plant originated from a cross-pollination in July, 2007 in Vleuten, The Netherlands of a proprietary selection of *Echinacea hybrida* identified as code number Ec 201-01, not patented, as the female, or seed, parent with a proprietary selection of *Echinacea hybrida* identified as code number Ec 558-05, not patented, as the male, or pollen, parent. The new *Echinacea* plant was discovered and selected by the Inventor as a single flowering plant from within the progeny of the stated cross-pollination grown in a controlled environment in Zuidwolde, The Netherlands in July, 2009.

Asexual reproduction of the new *Echinacea* plant by micropropagation a controlled environment in Heerhugowaard, The Netherlands since July, 2009, has shown that the unique features of this new *Echinacea* plant are stable and reproduced true to type in successive generations.

SUMMARY OF THE INVENTION

Plants of the new *Echinacea* have been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'Southern Belle'. These characteristics in combination distinguish 'Southern Belle' as a new and distinct *Echinacea* plant:

1. Upright plant habit.
2. Vigorous growth habit.
3. Freely basal branching habit.

4. Strong flowering stems.
5. Early and freely flowering habit.
6. Long flowering period.
7. Large anemone-type inflorescences with red purple-colored ray and disc florets.
8. Good garden performance.

Plants of the new *Echinacea* can be compared to plants of the female parent selection. Plants of the new *Echinacea* differ from plants of the female parent selection in the following characteristics:

1. Plants of the new *Echinacea* are shorter than plants of the female parent selection.
2. Plants of the new *Echinacea* are more freely flowering than plants of the female parent selection.
3. Ray florets of plants of the new *Echinacea* are not as drooping as ray florets of plants of the female parent selection.

Plants of the new *Echinacea* can be compared to plants of the male parent selection. Plants of the new *Echinacea* differ from plants of the male parent selection in the following characteristics:

1. Plants of the new *Echinacea* are taller than plants of the male parent selection.
2. Plants of the new *Echinacea* and the male parent selection differ in inflorescence form.

Plants of the new *Echinacea* can be compared to plants of *Echinacea hybrida* 'Razzmatazz', disclosed in U.S. Plant Pat. No. 13,894. In side-by-side comparisons, plants of the new *Echinacea* differed from plants of 'Razzmatazz' primarily in the following characteristics:

1. Plants of the new *Echinacea* had smaller leaves than plants of 'Razzmatazz'.
2. Plants of the new *Echinacea* flowered earlier than plants of 'Razzmatazz'.
3. Plants of the new *Echinacea* flowered for a longer period of time than plants of 'Razzmatazz'.
4. Ray florets of plants of the new *Echinacea* were not as drooping as ray florets of plants of 'Razzmatazz'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Southern Belle' grown in a container.

The photograph on the second sheet is a close-up view of typical inflorescences of 'Southern Belle'.

The photograph on the third sheet is a close-up view of the upper surface of a typical leaf and stem of 'Southern Belle'.

DETAILED BOTANICAL DESCRIPTION

The aforementioned photographs and following observations and measurements describe plants grown during the late summer in an outdoor nursery in Zuidwolde, The Netherlands and under conditions and practices which approximate those generally used in commercial *Echinacea* production. During the production of the plants, day temperatures ranged from 15° C. to 32° C. and night temperatures ranged from 8° C. to 18° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Southern Belle'.

Parentage:

*Female parent*.—Proprietary selection of *Echinacea hybrida* identified as code number Ec 201-01, not patented.

*Male parent*.—Proprietary selection of *Echinacea hybrida* identified as code number Ec 558-05, not patented.

Propagation:

*Type*.—By micropropagation.

*Time to initiate roots, summer*.—About one week at 25° C.

*Time to produce a rooted young plant, summer*.—About five weeks at 21° C.

*Root description*.—Fine, fibrous; pale cream in color.

*Rooting habit*.—Freely branching; moderately dense.

Plant description:

*Plant form/growth habit*.—Herbaceous perennial; upright and columnar plant habit, narrow inverted triangle; freely basal branching habit; vigorous growth habit.

*Plant height*.—About 110 cm.

*Plant diameter or spread*.—About 47.3 cm.

*Basal branches*.—Length: About 52.7 cm. Diameter: About 4 mm. Internode length: About 6.3 cm. Aspect: Erect to about 30° from vertical. Strength: Strong. Texture: Pubescent, strigose; rough. Color: Close to 146B to 146C strongly tinged with between 183A and 187B.

Foliage description:

*Arrangement*.—Alternate, simple.

*Length*.—About 11.9 cm.

*Width*.—About 3.6 cm.

*Shape*.—Narrowly ovate.

*Apex*.—Acute.

*Base*.—Attenuate to cuneate.

*Margin*.—Entire; undulate.

*Texture, upper and lower surfaces*.—Densely pubescent, strigose; rough.

*Venation pattern*.—Pinnate.

*Color*.—Developing leaves, upper surface: Close to 137B. Developing leaves, lower surface: Close to 137B to 137C. Fully expanded leaves, upper surface: Close to 137A; venation, close to 144C. Fully expanded leaves, lower surface: Close to 137C; venation, close to 145B to 145C.

*Petioles*.—Length: About 6.3 cm. Diameter: About 2 mm. Texture, upper surface: Smooth, glabrous. Texture, lower surface: Pubescent, strigose. Color, upper surface: Close to 144B. Color, lower surface: Close to 144C.

Inflorescence description:

*Appearance*.—Rotate anemone-type inflorescence form with ray and disc florets arranged acropetally on a capitulum; inflorescences positioned upright above the foliar plane on strong peduncles.

*Quantity of inflorescences per plant*.—About 15.

*Fragrance*.—None detected.

*Time to flower*.—Plants flower continuously from early July to late September in The Netherlands.

*Inflorescence longevity*.—Inflorescences maintain good substance for about three weeks on the plant; inflorescences not persistent.

*Inflorescence bud*.—Height: About 1.8 cm. Diameter: About 2.7 cm. Shape: Flattened globular. Color: Close to 143A.

*Inflorescence size*.—Diameter: About 10.1 cm. Depth (height): About 5.8 cm. Disc diameter: About 7.5 cm. Receptacle height: About 1.3 cm. Receptacle diameter: About 1.2 cm. Receptacle color: Close to NN155A.

*Ray florets*.—Length: About 5.2 cm. Width: About 1.2 cm. Shape: Narrowly oblanceolate. Apex: Praemorse. Base: Cuneate. Margin: Entire. Texture, upper and lower surfaces: Smooth, glabrous, longitudinally ridged. Number of ray florets per inflorescence: About 20 arranged in a single whorl. Aspect: Horizontal to slightly drooping, about 30° from horizontal. Color: When opening, upper surface: Close to 63B. When opening, lower surface: Close to 58A. Fully opened, upper surface: Close to 64A to 64B; color becoming closer to 71A to 71B with development. Fully opened, lower surface: Close to 59C; color becoming closer to 64A with development.

*Disc florets*.—Length: About 3.4 cm. Diameter: About 8 mm. Shape: Tubular, enlarged; apices praemorse. Number of disc florets per inflorescence: About 220. Texture, upper and lower surfaces: Smooth, glabrous. Color: Immature, inner surface: Close to 53A to 53B. Immature, outer surface: Close to 58A. Mature, inner surface: Between 64B and 67B. Mature, outer surface: Close to 59C.

*Receptacle spines*.—Quantity: One per disc floret. Shape: Acicular. Apex: Acute. Base: Attenuate. Texture: Smooth, glabrous. Color: Apex: Close to 183A to 183B. Mid-section: Close to 144B. Base: Close to 150D.

*Involucral bracts*.—Quantity per inflorescence: About 50 arranged in about three whorls. Length: About 9 mm. Width: About 3.5 mm. Shape: Ovate. Apex:

Acute. Base: Cuneate. Margin: Entire. Texture, upper surface: Smooth, glabrous. Texture, lower surface: Sparsely pubescent along the margins. Color, upper surface: Close to 137A to 137B; towards the base, close to 143B to 143C. Color, lower surface: Close to 137B.

*Peduncles*.—Length, terminal peduncle: About 18.9 cm. Diameter: About 6 mm. Strength: Strong. Aspect: Mostly upright. Texture: Pubescent, strigose. Color: Close to 183B.

*Reproductive organs*.—Androecium (present on disc florets only): Quantity per floret: About two, deformed. Filament length: About 1 mm. Filament color: Close to N155B to N155C. Anther shape: Oblong. Anther length: About 2 mm. Anther color: Close to N199B. Pollen amount: None observed. Gynoecium (present on ray and disc florets): Quantity per floret: One. Pistil length: About 1.2 cm. Stigma shape: Decurrent. Stigma color: Close to 63B. Style length: About 1.1 cm. Style color: Close to 62D. Ovary color: Close to 157A to 157B. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good garden performance and tolerate rain and wind. Plants of the new *Echinacea* have been observed to tolerate high temperatures of about 35° C. and hardy to USDA Hardiness Zone 4.

It is claimed:

1. A new and distinct *Echinacea* plant named 'Southern Belle' as illustrated and described.

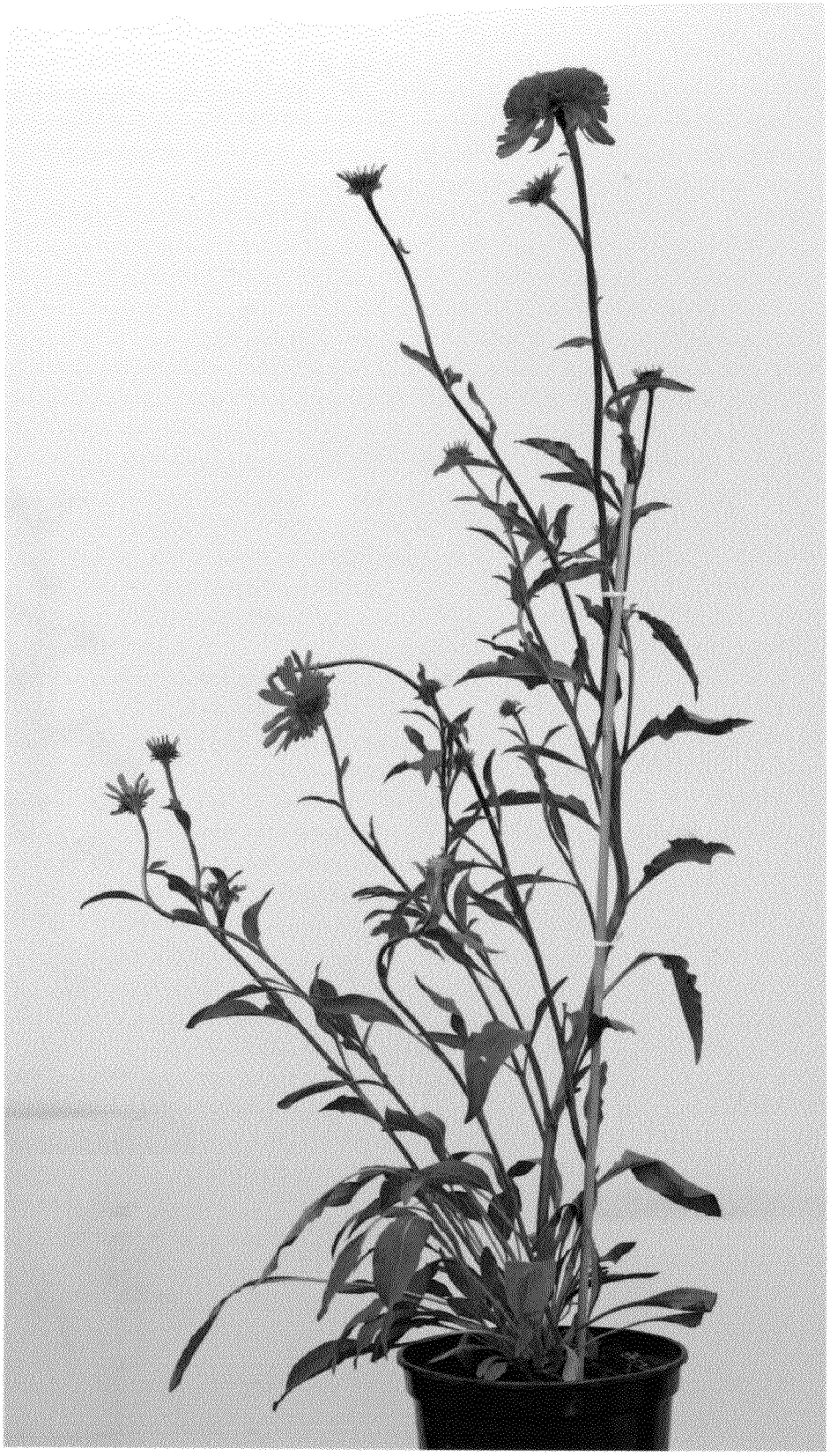

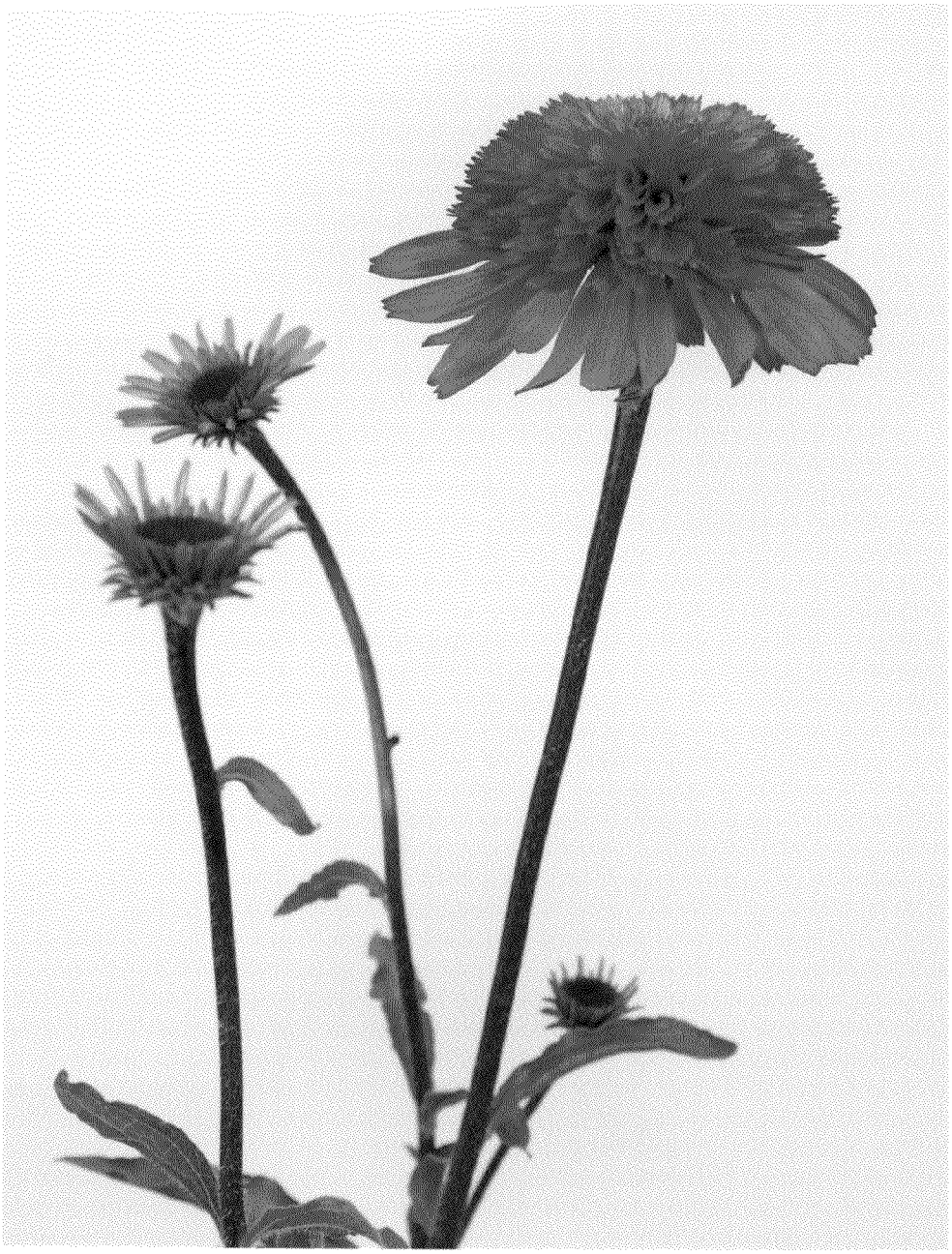

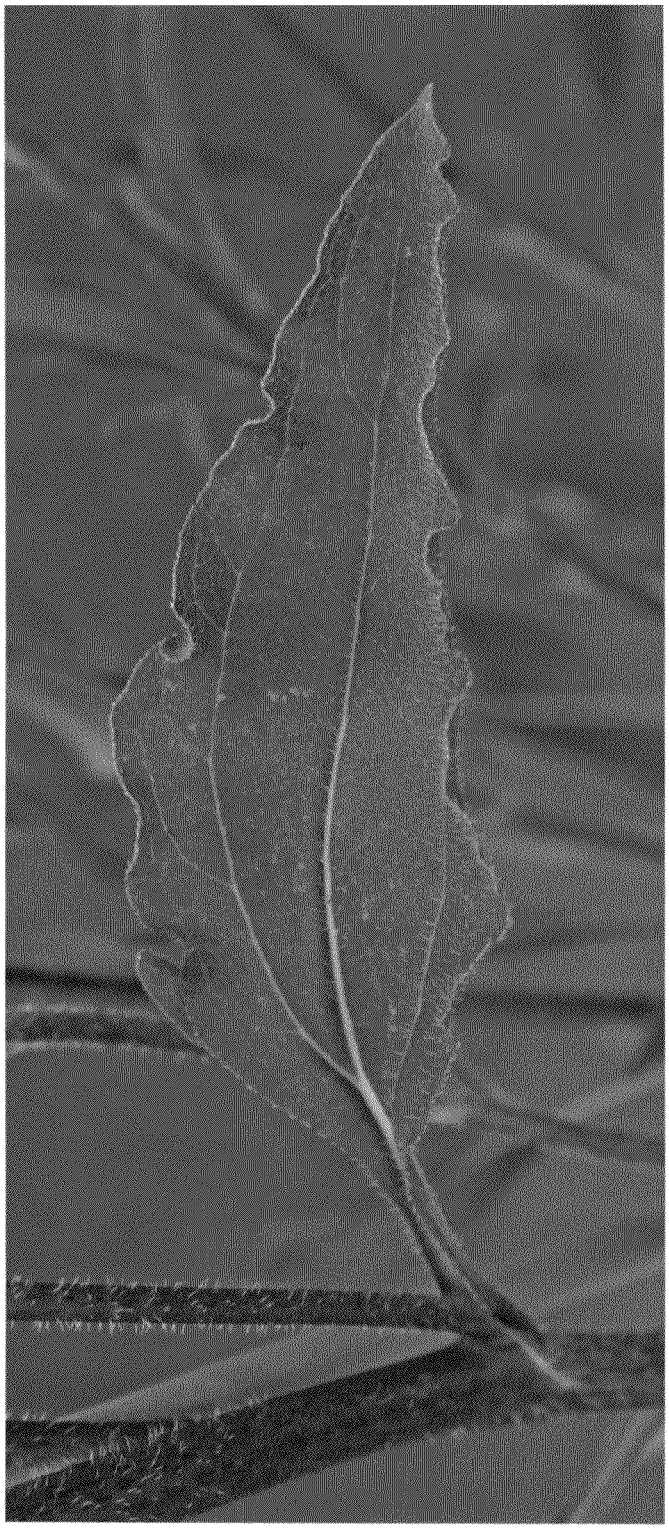

* * * * *